United States Patent
Schenker et al.

(10) Patent No.: US 8,701,675 B1
(45) Date of Patent: Apr. 22, 2014

(54) LASER TREATMENT FOR CNS INJURY

(75) Inventors: Samuel D. Schenker, Toms River, NJ (US); Arthur Dale Ericsson, Houston, TX (US)

(73) Assignee: Samuel D. Schenker, Toms River, NJ (US)

( * ) Notice: Subject to any disclaimer, the term of this patent is extended or adjusted under 35 U.S.C. 154(b) by 85 days.

(21) Appl. No.: 13/216,108

(22) Filed: Aug. 23, 2011

Related U.S. Application Data

(60) Provisional application No. 61/376,033, filed on Aug. 23, 2010.

(51) Int. Cl.
*A61N 5/067* (2006.01)

(52) U.S. Cl.
USPC .............. 128/898; 607/88; 607/89; 607/90; 607/91; 607/92; 607/93; 607/94

(58) Field of Classification Search
USPC ..................... 606/2–19; 607/88–95
See application file for complete search history.

(56) References Cited

U.S. PATENT DOCUMENTS

| | | | | |
|---|---|---|---|---|
| 4,671,285 A * | 6/1987 | Walker | | 607/89 |
| 5,445,608 A * | 8/1995 | Chen et al. | | 604/20 |
| 5,571,152 A | 11/1996 | Chen et al. | | |
| 6,551,346 B2 * | 4/2003 | Crossley | | 607/88 |
| 7,344,555 B2 * | 3/2008 | Anders et al. | | 607/89 |
| 2006/0155348 A1* | 7/2006 | deCharms | | 607/89 |

\* cited by examiner

*Primary Examiner* — Aaron Roane
(74) *Attorney, Agent, or Firm* — Chapin IP Law, LLC

(57) ABSTRACT

Techniques disclosed herein include systems and methods for treating spinal cord injury. Techniques include using a diode laser assembly, a power source, a fiber optic cable, and a fenestrated tip. The power source can be connected to the diode laser assembly, with a fiber optic cable connected to the diode laser assembly. The fenestrated tip is connected to the fiber optic cable to emit a plurality of laser light beams produced by the diode laser assembly at a location remote from the diode laser assembly. The apparatus can be used in a method for treating a spinal cord injury. The method is carried out by providing a source of laser light having a wavelength in the range of 500-1000 nm and a power in the range of 5 to 500 milliwatts. The laser light is transmitted through an optical wire to a position adjacent a spinal cord injury site, with at least a portion of the apparatus positioned within a human body. The spinal cord injury site is then irradiated with laser light from the optical wire.

17 Claims, 5 Drawing Sheets

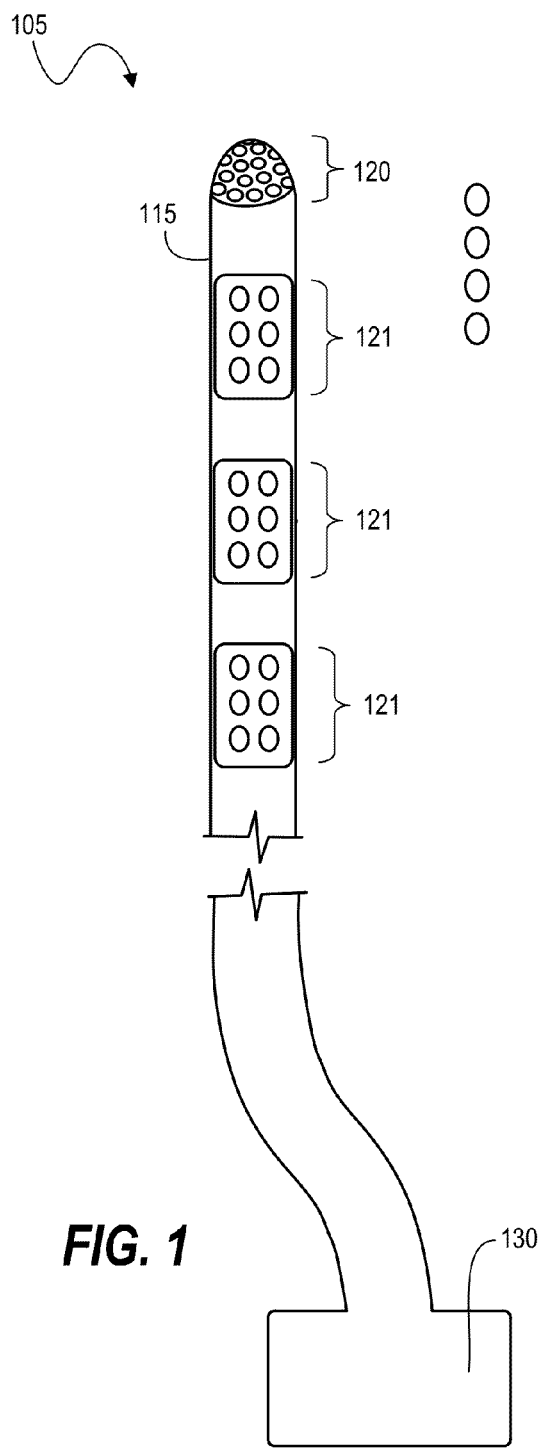
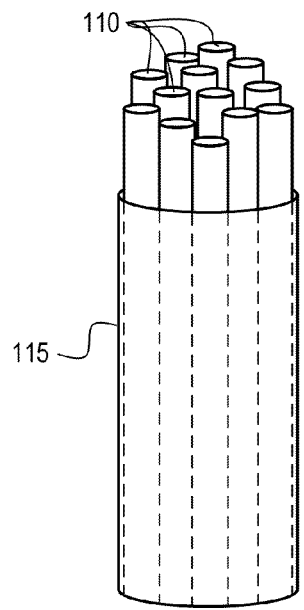
FIG. 2
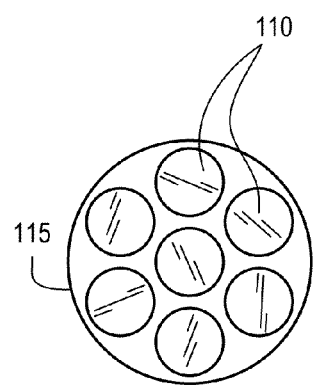
FIG. 3
FIG. 1

LASER TREATMENT FOR CNS INJURY

CROSS REFERENCE TO RELATED APPLICATIONS

The present application claims the benefit of U.S. Provisional Patent Application No. 61/376,033, filed on Aug. 23, 2010, entitled "Implanted Laser Treatment For Injuries," which is incorporated herein by reference in its entirety.

BACKGROUND

The present disclosure related to treating injuries, especially injuries to the central nervous system, such as spinal cord injuries.

The central nervous system (CNS) is an integral part of the biology of humans and animals. The central nervous system typically includes the combination of the brain and spinal cord. The CNS integrates information received from all parts of the body, and coordinates activity of body parts. Accordingly, a healthy CNS is crucial to proper functioning of a body. Injuries to the central nervous system, especially spinal cord injuries, can therefore inhibit and even prevent proper body functioning. For example, a CNS or spinal injury can result in pain, numbness, loss of sensation, unresponsive muscles, loss of connection between the brain and body, difficulty breathing, partial paralysis, and even complete paralysis.

Damage to the spinal cord can result from diseases and from physical trauma. Motor vehicle collisions, falls, sports injuries, and work-related accidents are common physical causes of spinal cord injury. Treatment of spinal cord injuries depends on type and severity of the injury itself. Treatments can include medication, surgery, and physical therapy.

SUMMARY

Conventional techniques for treating spinal cord injuries include direct exposure to laser light. Studies have shown that transcutaneous as well as direct exposure to laser light can assist in regenerating injured cells. Yet conventional techniques suffer from a variety of deficiencies. For example, U.S. Patent Application Publication Number 2006/0036299 (Feb. 16, 2006) discloses a transcutaneous treatment of a spinal cord injury (SCI) by applying low-power laser irradiation (LPLI). A drawback of this method, however, is that tissue penetration of laser light is only on the order of 0.05 cm for each watt of power input, and even less in bone. The relatively small amount of tissue penetration can lead to applying relatively high intensity light to the skin surface to provide adequate power to the site of the SCI. Unfortunately the high-intensity light on the skin surface can cause adverse effects. Another drawback is that the laser light is focused in a small area, requiring that the beam be reoriented from time to time, or that a second beam is used to help cover an entire site.

Accordingly, there is a desire for a more efficacious laser treatment of spinal cord injuries. Techniques disclosed herein provide a method and device that treats injuries to the central nervous system, including spinal cord injuries, by controlled exposure to laser light.

One embodiment includes a method for treating a spinal cord injury. The method includes using a source of laser light having a wavelength in the range of 500-1000 nm and a power in the range of 5 to 500 milliwatts. Laser light is transmitted through an optical wire or conduit to a position adjacent a spinal cord injury site. The spinal cord injury site is then irradiated with laser light from the optical wire.

Another embodiment of the invention includes an apparatus comprising a diode laser assembly, a power source, a fiber optic cable, and a fenestrated tip. The power source is connected to the diode laser assembly. The fiber optic cable is connected to the diode laser assembly. The fenestrated tip is connected to the fiber optic cable to emit a plurality of laser light beams produced by the diode laser assembly at a location remote from the diode laser assembly. Such a laser device can be implantable.

Of course, the order of discussion of the different steps as described herein has been presented for clarity sake. In general, these steps can be performed in any suitable order.

As discussed above, techniques herein are well suited for use in CNS and spinal cord injury treatments. It should be noted, however, that embodiments herein are not limited to use in such applications and that the techniques discussed herein are well suited for other applications as well.

Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Note that this summary section herein does not specify every embodiment and/or incrementally novel aspect of the present disclosure or claimed invention. Instead, this summary only provides a preliminary discussion of different embodiments and corresponding points of novelty over conventional techniques. For additional details and/or possible perspectives of the invention and embodiments, the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein as illustrated in the accompanying drawings in which like reference characters refer to the same parts throughout the different views. The drawings are not necessarily to scale, with emphasis instead being placed upon illustrating the embodiments, principles and concepts.

FIG. 1 is an example laser light device according to embodiments herein.

FIG. 2 is an example section of a laser light device according to embodiments herein.

FIG. 3 is a cross sectional view of an example laser light device according to embodiments herein.

DETAILED DESCRIPTION

Figure 4:
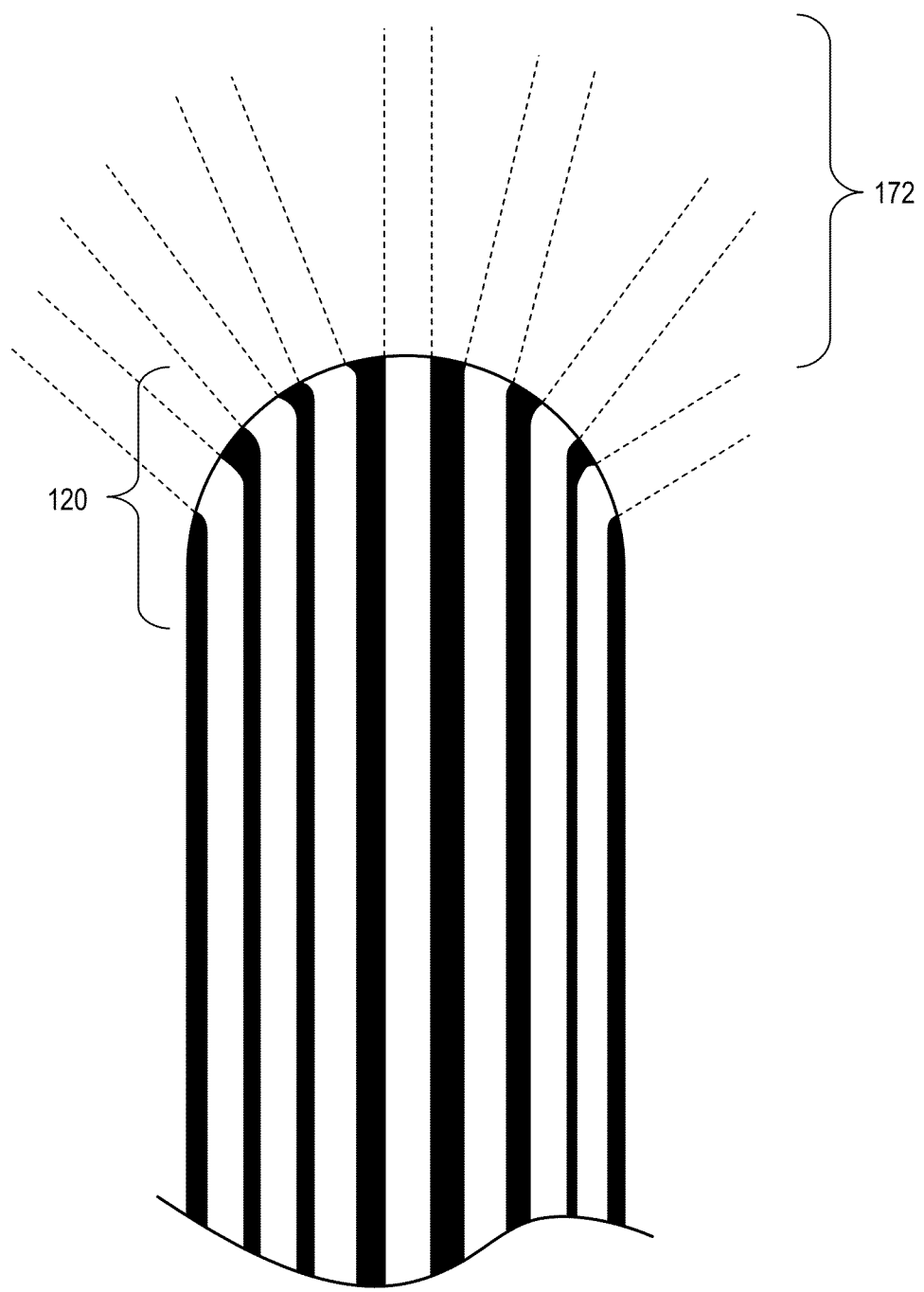
FIG. 4 is a longitudinal sectional view of an example laser light device according to embodiments herein.

Techniques disclosed herein provide a method and device that treats injuries to the central nervous system, including spinal cord injuries, by controlled exposure to laser light.

One embodiment includes a method for treating a spinal cord injury. The method includes using a source of laser light having a wavelength in the range of 500-1000 nm and a power in the range of 5 to 500 milliwatts. Laser light is transmitted through an optical wire or conduit to a position adjacent to a spinal cord injury site. The spinal cord injury site is then irradiated with laser light from the optical wire.

Preferably, the source of laser light provides light having a wavelength in the range of 730-830 nm and a power delivery in the range of 15 to 90 milliwatts. More specifically, the source of laser light can selectively emit a laser light having a wavelength selected from one of a multiplicity of accessible wavelengths from within the 730 to 830 nm range, and selectively emit a laser light having a power selected from one of a multiplicity of accessible power levels from within the 15 to 100 milliwatt range. Note that at about 830 nm, light absorption in nerve cells, dermis, and hemoglobin is optimal.

There are several cellular effects that can result from wavelengths around 830 nm. For example, one effect is stabilization of cellular mitochondrial membranes with measurements of Ca, Na, and K ion gradients. Adenosine-triphosphate (ATP) production is enhanced, thereby providing energy for cell replication, repair and peptide production. Cellular release of histamine, serotonin and CO2 produces additional vasodilatation and increased blood flow and levels of INF-g. This increased blood flow can be further increased by prostaglandin synthesis. There is also a reduction of the IL 1 and TNF improved anti-inflammatory effect on cells. A reduction of inflammation induces normal function of the astrocyte neuron lactate shuttle, and thus increases the efficacy of lactate for use by neuronal mitochondria for ATP production. This increased ATP production stabilizes intracellular water polarization onto protein organelles (actin and microtubules), thus impeding cell death. Cellular effects also include a decrease of inflammatory cellular response by production of TH2 T cells and superoxide dismutase, as well as non-specific effects of an 830 nm laser on other inflammatory markers such as C reactive protein, macrophage production, neo-vascularation, fibroblast proliferation, epithelial cell regeneration, and increase in DNA synthesis.

The optical wire can be comprised of a plurality of optical fibers. The optical wire can also be terminated by a fenestrated tip and encased in a sheath that that covers the plurality of optical fibers, and that extends from the tip. A number of optical fibers included in the plurality can be any suitable or feasible number. The number can depend on various factors such as optical wire thickness, available power, sheathing constraints, etc. The number can also be arbitrarily selected. For example, the optical fibers can be between 10 and 100 in number. The fenestrated tip can have a window opening for transmission of laser light from each of the optical fibers. In other embodiments, the fenestrated tip can have window openings for emitting laser light at an angle from a longitudinal axis of the tip. For example, the fenestrated tip can have window openings in a rounded end face of the tip for emitting a plurality of laser light beams in a spreading axial pattern from the tip, or window openings through a sidewall of the tip for emitting a plurality of laser light beams laterally from the tip.

In one technique, the tip can be placed in a position adjacent to a given spinal cord injury site and within two cm of the injury, and even within one cm of the injury. The tip can also be positioned subcutaneously or, alternatively, in an epidural space either alongside the injury or pointed toward the injury. Exact orientation can depend on a particular configuration of the tip. In some embodiments, the source of laser light can be implanted in the patient. Implanting the laser light in the patient can be beneficial as a means for relief from chronic pain.

Another embodiment of the invention includes an apparatus comprising a diode laser assembly, a power source, a fiber optic cable, and a fenestrated tip. The power source is connected to the diode laser assembly. The fiber optic cable is connected to the diode laser assembly. The fenestrated tip is connected to the fiber optic cable to emit a plurality of laser light beams produced by the diode laser assembly at a location remote from the diode laser assembly. Such a laser device can be implantable.

The fenestrated tip can have a plurality of window openings in a rounded-end face of the tip for emitting a plurality of laser light beams in a spreading axial pattern from the tip. In another preferred embodiment of the invention, the fenestrated tip has a plurality of window openings through a sidewall of the tip for emitting a plurality of laser light beams laterally from the tip.

Figures 7, 8:
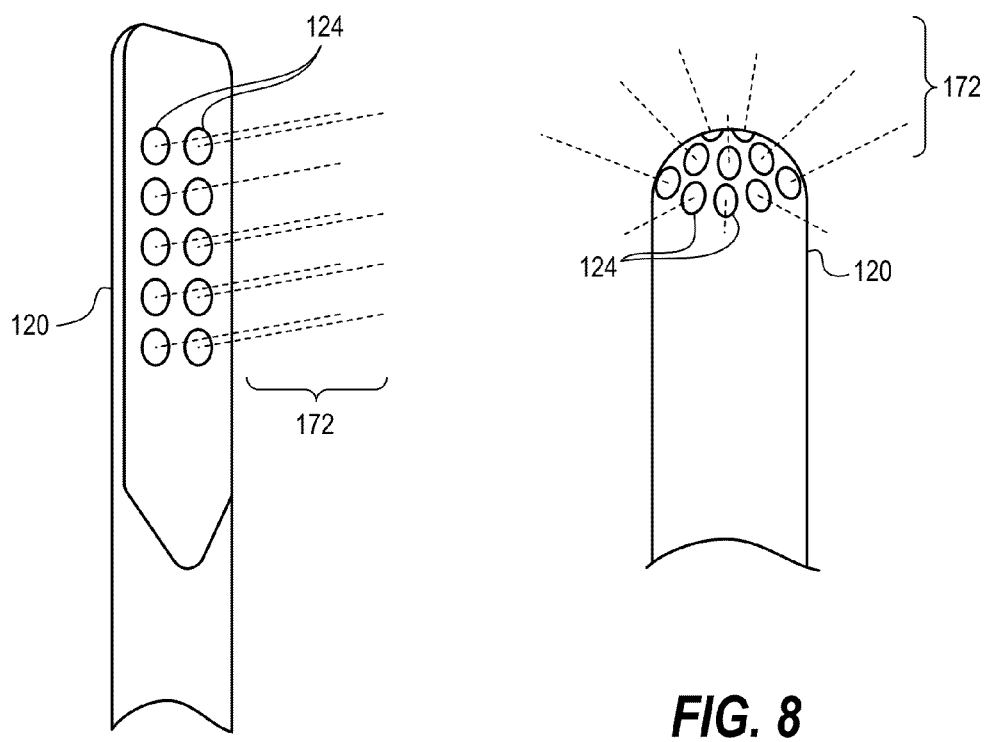
FIG. 7 is a diagram of a tip section of a laser light device according to embodiments herein.
FIG. 8 is an example end view of a tip of a laser light device according to embodiments herein.

Referring now to FIGS. 1-4, an optical fiber bundle can comprise a plurality of optical fibers 110 bundled or aligned parallel to each other, and can then terminate at a fenestrated tip section 120. FIG. 2 shows an example bundle of optical fibers 110, which can be encased within a sheath 115 or other covering. The sheath 115 can extend from a tip section of a bundle to a diode laser assembly 130, thereby covering the bundle. A number of optical fibers selected can vary on application of the apparatus. For example, in some embodiments, the bundle can include between two and one hundred optical wires or more. In other particular embodiments, a number of optical wires between three and twenty can be beneficial. FIG. 1 illustrates a laser treatment apparatus 105 having an implantable electronics pack 130 and a fenestrated tip section 120. The fenestrated tip section 120 can include one or more window openings for transmission of laser light from each optical fiber included in the bundle. In some embodiments, the fenestrated tip section 120 can include window openings for emitting laser light at an angle, or at a plurality of angles, such as from a longitudinal axis of the tip section. For example, the fenestrated tip section can have window openings in a rounded-end face of the tip section adapted for emitting a plurality of laser light beams in a spreading axial pattern from a tip section. FIG. 4 shows a sectional view of an example tip section with an axial spreading pattern. In another embodiment, window opening can be defined through a sidewall of the tip section for emitting a plurality of laser light beams laterally from the tip section. An example of a tip having a lateral light emission pattern is shown in FIG. 7.

FIG. 1 also shows sidewalls 121. Particular embodiments can include one or more sidewalls in addition to a tip or in place of a fenestrated tip. Such sidewalls 121 can be thought of as paddles or bands, which are laser light emission surfaces along an optical fiber or optical fiber bundle to emit a portion of the laser light. Each laser light emission surface can include one or more apertures, lenses, or other light transmission points to emit laser light carried by one or more fiber optic lines. A number an size of light transmission points can be dependent on a particular application. For example, for small lesions a given sidewall may contain only a handful of transmission points, while for larger lesions the sidewall can span an inch or two in length and have dozens of transmission points. Having more light transmission points then needed can help increase regeneration, and account for movement of the device within a human body. In other embodiments, the sidewall area can span several inches to cover a large legion. Alternatively, several sidewalls can be used at strategic points By way of a non-limiting example, an outside diameter of an optical fiber bundle and sheath (the combination being referred to as a catheter) for insertion in a spinal column can be in the range of about 0.3 to 0.6 cm, with about 3-20 optical fibers. Each optical fiber generally carries laser light at a power in the range of 1-30 watts. An example catheter can have a length of about 5-50 cm. Note that these specifications can be modified depending on a particular application.

Figure 5:
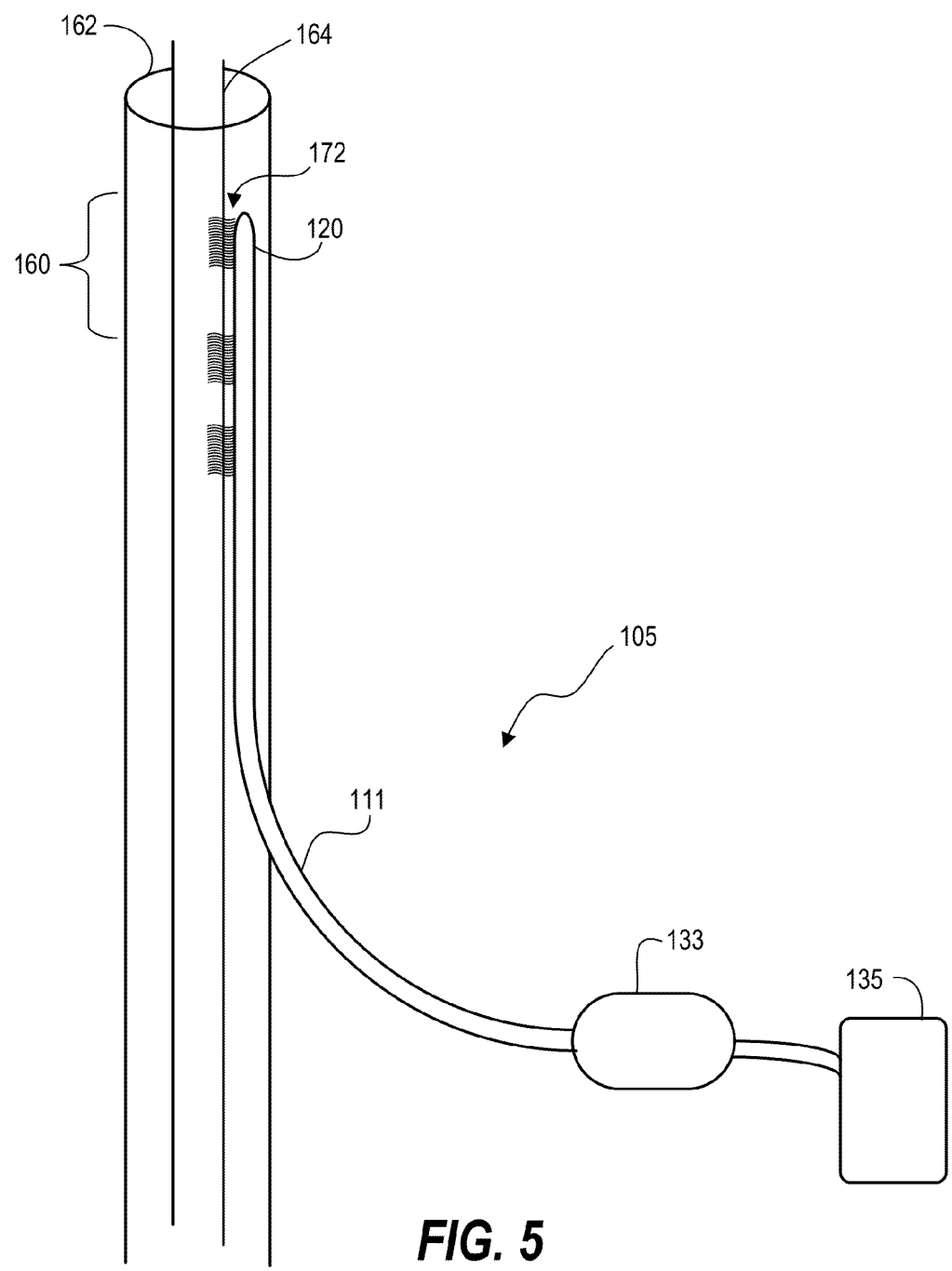
FIG. 5 is a schematic diagram of a laser light system for treating a spinal cord injury according to embodiments herein.
Figure 6:
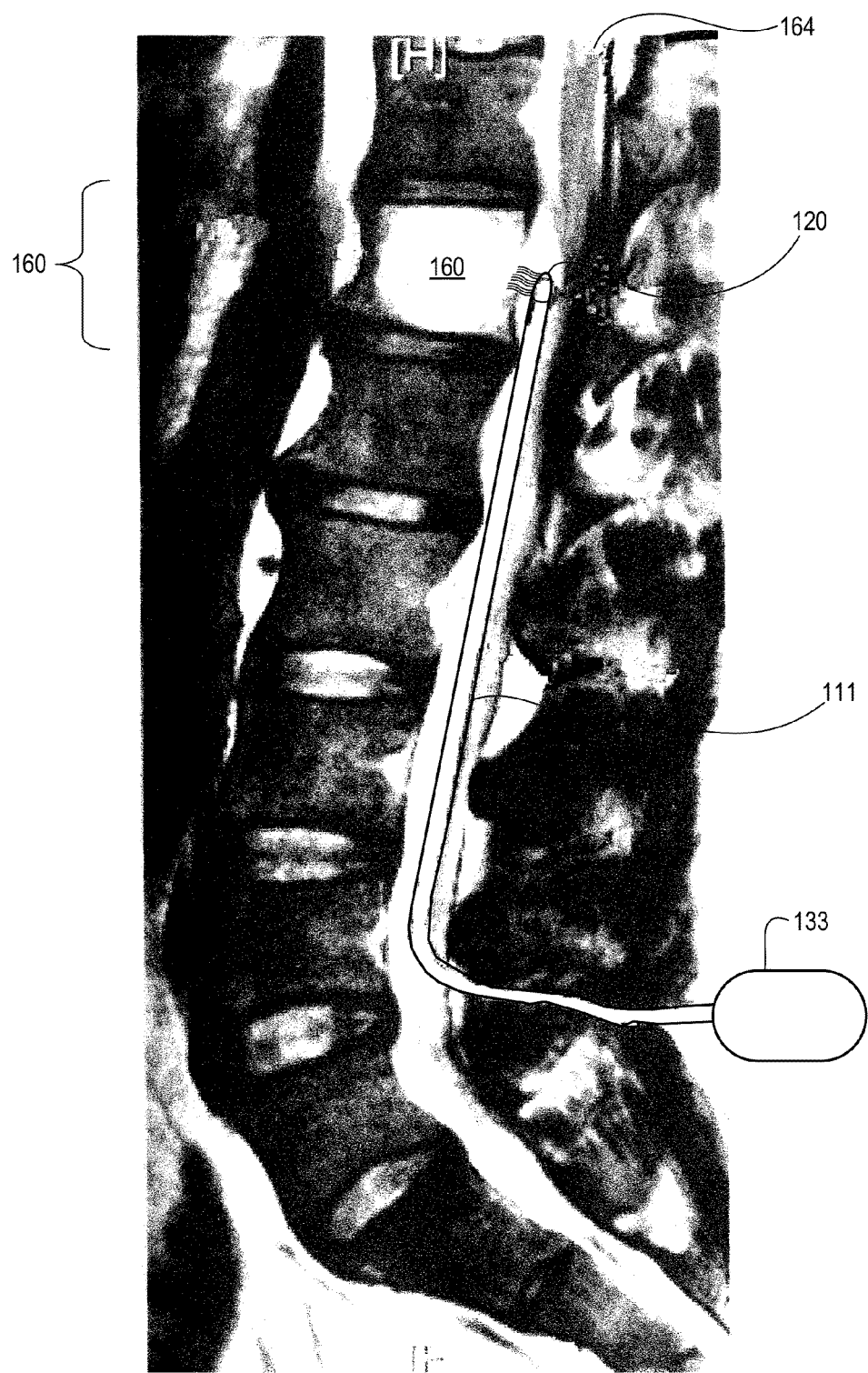
FIG. 6 is a diagram showing positioning of a laser light device in a patient for treatment of a spinal cord injury according to embodiments herein.

FIGS. 5 and 6 show a diagram illustrating placement of a laser treatment device. During treatment of a spinal cord injury, a tip section can be positioned adjacent to a spinal cord injury site 160. Treatment can include positioning windows of the fenestrated tip within about two centimeters of at least a portion of the injury, and can include positioning the tip within about one centimeter of the injury. In some embodiments, the tip section can be positioned subcutaneously. In some treatment conditions, however, placement can be more effective in other locations. For example, an alternative placement location is the epidural space between dura mater 162 and the spinal cord 164. Placement can either be alongside the injury or longitudinally spaced from the injury, but with the windows pointed toward the injury site 160, depending on a given tip configuration. In other words, the tip can be positioned so that laser light 172 impinges the injury. Optionally, the source of the laser light can be implanted within a patient, such as when a purpose of placement is relief from chronic pain or an extended treatment cycle.

In another embodiment, a laser treatment apparatus 105 comprises a diode laser assembly 133, a power source 135, optical fiber bundle 111, and a fenestrated tip section 120. The fenestrated tip section 120 can be connected to the fiber optic cables and adapted to emit a plurality of laser light beams produced by the diode laser assembly, but at a location relatively remote from the diode laser assembly.

Referring now to FIGS. 3 and 4, the fenestrated tip section 120 can have a plurality of window openings 124 in a rounded-end face of the tip section for emitting a plurality of laser light 172 in a spreading axial pattern from the tip section. In another embodiment, the fenestrated tip section 120 has a plurality of window openings 124 through a sidewall of the tip section for emitting multiple laser light 172 laterally from the tip section.

Returning to FIGS. 1-3, a 730-930 nm laser treatment apparatus 105 can be introduced into the epidural space via an insulated fiber optic cable, adapted to deliver a current (e.g. 15-90 milliwatts), through a fenestrated tip 120 at the end of the fiber optic sheath 115. A catheter can be directed under fluoroscopic guidance to a region of suspected trauma or lesion. FIG. 6 shows an example of such fluoroscopic guidance. FIG. 6 shows an apparatus similar to that shown in FIG. 5, but with placement along a spine to provide adjacent emission of laser light. Once the region is determined, the device can be implanted subcutaneously. Electronics pack 130 or generator (which can comprise the diode laser and battery pack or other power source) can also be implanted and attached to the cable as a source of energy. Note that transcutaneous as well as direct exposure to laser light can be useful in the course of regenerating nerve cells. In an additional technique, directing the laser beam to multi-synaptic pain pathways can help relieve chronic pain. For chronic pain applications, the laser light therapy can be used more for stimulation rather than cellular regeneration.

By way of a non-limiting example, one particular example device can include a triple diode laser configured to deliver an output of several frequencies and power settings. For example, a given device can emit at 760 nm, 810 nm and/or 830 nm laser emission, with power settings of 15 mW, 30 mW, 60 mW, and 90 mW. Tissue penetration is typically 0.05 cm per each mw output at each of the laser frequencies. Such a laser diode can be affixed on a base of an insulated fiber sterile cable. This cable can be attached to the diode laser, which can have a plug-in power source configured to be inserted in a tissue pocket formed in a patient. Alternatively, a laser diode array can be used in conjunction with multiple fiber optic lines.

The fiber optic cable effectively carries the laser light directly to tissues to be lased. The diode laser can have a programmable controller to deliver 1,589 Joules/cm squared per day to an area of damage. This particular laser dosage can provide effective neuronal regeneration. Regarding notation, Energy (Joule)=Mean Power (W)×Time (sec). Also, Energy=30 mW×33 Sec=0.99 Joule.

Regarding placement, under fluoroscopic control, the fiber optic catheter can be placed in juxtaposition of the spinal cord, nerve root or other tissue that has been damaged and sutured in place. Example devices can be used to regenerate other tissues besides the spinal cord, such as brain tissue, with placement of the device in corresponding areas of the body. In one example, the diode laser can be attached and a battery pack placed in position and sutured in order to provide maximum protection and fixed placement.

Use of a "cold laser" with frequencies of 760, 810 and/or 830 nm with energy output of 30, 60 or 90 mW can result in axonal and functional regeneration of injured neurons in peripheral nerves, nerve roots and in the spinal cord following injury and/or hemisection or transaction. The depth of penetration of a given laser beam can depend upon frequency (nm) and output (mW). Optimal soft tissue penetration in some humans is between 670 nm and 850 nm. Proper laser power penetration of the nerve tissue of the spinal cord can significantly increase axonal re-growth leading to functional recovery following significant spinal cord damage. This process will be vitally important in trauma to the spinal cord following diving accidents, automobile accidents, sports injuries and other trauma. In addition, specific anterior lateral spinal cord placement of the laser light can be useful in blocking chronic pain syndromes and severe intractable pain syndromes associated, for example, with metastatic cancer.

One embodiment includes a method for treating an internal bodily injury (such as a spinal cord injury). The method includes providing a source of laser light having a wavelength in the range of 500-1000 nm and a power in the range of 5 to 500 milliwatts. The method includes transmitting the laser light through an optical wire, with the laser light being transmitted from the source of the laser light to a location adjacent to a bodily injury site. The optical wire is connected to a light emission surface positioned adjacent to the spinal cord injury site. The light emission surface is adapted to emit laser light from the optical wire to the spinal cord injury site. The light emission surface can be a lens, window, aperture, or simply the end of a fiber optic wire (with the end surface oriented approximately perpendicular to a longitudinal direction of the optical wire such that light escapes the optical wire at that point). The light emission surface can include multiple light emission points. The light emission surface and at least a portion of the optical wire are positioned within a human body. The method then includes irradiating the bodily injury site with the laser light carried via the optical wire.

In other words, the method includes treating a spinal cord injury site with laser light from within the human body, that is, the laser light is emitted onto/into an injury site from a location within the human body, thereby assisting cellular regeneration. Conventional laser treatments are external to the body and powered to destroy cellular or bodily structures, whereas techniques disclosed herein use laser treatment for regeneration, with internal emission to directly heal neuropathways.

In various alternative embodiments, the source of laser light can have a wavelength in the range of 730-830 nm and a power in the range of 15 to 90 milliwatts, which can provide better results in some applications. The light emission surface can be positioned within about 2 centimeters of the injury site or positioned within about 1 centimeter of the injury site. The optical wire and light emission surface(s) can be positioned subcutaneously, positioned in the epidural space of a human spinal canal, positioned near the brain stem, cranial nerves, eye nerves, facial nerves, positioned within or next to organs, etc.

The method can include implanting the source of laser light, optical wire, and tip all within the human body. Placement within the body can be either temporary or indefinite. For example, for treating acute injuries, treatment can include implanting the laser light apparatus within the body for a few months to half a year or year, after which the apparatus can be removed. For treating chronic conditions, the apparatus can be left in the body indefinitely, including implanting a battery source. The battery source can be configured with a rechargeable battery that can be recharged externally using a wireless power charger. External recharging means no surgical replacement of the battery after losing a charge. For spinal cord placement, placement can be in front of the spine, in back of the spine or other area within the body. Placement can be executed using a catheter and/or in combination The source of laser light can selectively emits a laser light having a wavelength selected from one of multiple selectable wavelengths. For example, there can be several predetermined laser settings, on or more of which a surgeon can select prior to positioning and implanting the device. Other embodiments include wireless tuning of the laser light via a remote control. This can include turning off the laser, selecting a light pattern (pulsed, continuous, etc.), and selecting or adjusting wavelength and power output from multiple selectable power levels.

The optical wire can comprise a plurality of optical fibers grouped or bundled together. The bundled optical fibers can extend from the laser source to the injury site. Alternatively, a bundle of optical fibers extends from a single fiber at or near an emission tip of the device. In particular embodiments, a number of optical fibers in the plurality of optical fibers can be between 10 and 100.

In another embodiment, the method includes emitting the light using a fenestrated tip or other light diffusion mechanism. The fenestrated tip can have an emission surface(s) for transmission of laser light from each of the optical fibers. Emission surfaces can be adapted for emitting the laser light at an angle relative to a longitudinal axis of the fenestrated tip. The fenestrated tip can be embodied as a rounded end that defines light emission openings, windows, or lenses in the fenestrated tip. These light emission openings can be configured to emit a plurality of laser light beams in a spreading axial pattern relative to the fenestrated tip. Having broad laser light emission coverage assists in keeping laser light flooding an injury site despite minor movements in positioning caused by movement of a corresponding human body. Alternatively, the fenestrated tip includes a sidewall that defines light emission openings in the fenestrated tip, with the light emission openings configured to emit a plurality of laser light beams from the sidewall. Other embodiments can include a sheath that covers the optical fibers from the first end of the optical fibers to the second end of the optical fibers, that is, from the laser source to a laser light emission point or diffusion tip.

Another embodiment includes a method for treating a spinal cord injury, a brain injury, or other nerve injury. This method includes providing a source of laser light having a wavelength in the range of 500-1000 nm and a power in the range of 5 to 500 milliwatts. The laser light can come from a diode laser or other laser generator with a battery or other power supply. The generated laser light is transmitted through an optical wire to a location adjacent to a spinal cord injury site. The optical wire has a first end and a second end. The first end of the optical wire is connected to the source of the laser light (such as a diode laser apparatus), while the second end of the optical wire is adapted to emit the laser light from the optical wire to the spinal cord injury site. The second end can thus have a terminal, lens, or other emission surface that permits the laser light to be emitted from the optical wire to the injury site. The second end of the optical wire, and at least a portion of the optical wire, are positioned within a human body, that is, at least under the skin surface of a human body. The method then includes irradiating the spinal cord injury site with the laser light carried via the optical wire.

In another embodiment, an injury treatment apparatus includes a diode laser assembly, a power source connected to the diode laser assembly, a fiber optic cable connected to the diode laser assembly, and a light emission surface connected to the fiber optic cable. The light emission surface is adapted to emit a plurality of laser light beams produced by the diode laser assembly. The laser light beams are emitted at a location remote from the diode laser assembly. The light emission surface is adapted to be positioned within a human body. The light emission surface can includes a plurality of laser light emission surfaces, in a rounded-end face of a fenestrated tip, and configured to emit a plurality of laser light beams in a spreading axial pattern relative to the fenestrated tip. Alternatively, the light emission surface includes a plurality of light emission surfaces, in a sidewall of the fiber optic cable, configured to emit a plurality of laser light beams laterally relative to the fiber optic cable.

In another embodiment, a laser therapy treatment device can include a diode laser assembly, a power source connected to the diode laser assembly, a fiber optic cable connected to the diode laser assembly, and one or more laser light emission surfaces located along the fiber optic cable, such as at an end of the fiber optic cable, or at various points along a sheath containing the fiber optic cable or fiber optic cable bundle. Alternatively a fenestrated tip is connected to the fiber optic cable adapted to emit a plurality of laser light beams produced by the diode laser assembly. The laser light beams are emitted at a location remote from the diode laser assembly. The fenestrated tip or side paddle/emission surfaces can be adapted to be positioned within a human body. Each side surface can have one or more lenses, apertures, or windows for laser light to be emitted. In some embodiments, the fenestrated tip can defines a plurality of laser light emission surfaces, in a rounded-end face of the fenestrated tip, that are configured to emit a plurality of laser light beams in a spreading axial pattern relative to the fenestrated tip. Alternatively, the device can include a plurality of light emission surfaces along a fiber optic line or sheath on a sidewall of the fiber optic line. Each side surface can define apertures or contain lenses/light emission surfaces that emit a plurality of laser light beams laterally relative to a fiber optic laser light transmission line.

Those skilled in the art will also understand that there can be many variations made to the operations of the techniques explained above while still achieving the same objectives of the invention. Such variations are intended to be covered by the scope of this invention. As such, the foregoing description of embodiments of the invention are not intended to be lim-

The invention claimed is:

1. A method for treating a spinal cord injury, the method comprising:
   providing a source of laser light having a wavelength in the range of 730-830 nm and a power in the range of 15 to 90 milliwatts;
   transmitting the laser light through an optical wire, the laser light being transmitted from the source of the laser light to a location adjacent to a spinal cord injury site, the optical wire connected to a light emission surface positioned adjacent to the spinal cord injury site, the light emission surface adapted to emit laser light from the optical wire to the spinal cord injury site, the light emission surface and at least a portion of the optical wire being positioned within a human body;
   disposing a plurality of the optical wires in a bundle, each of the optical wires terminating in a window defining the light emission surface;
   arranging a subset of the windows in a sidewall of a fenestrated tip, the sidewall facing the spinal cord injury site;
   arranging a subset of the windows in a rounded end face, the rounded ended face orienting the windows in an axial spreading pattern directed toward the spinal cord injury site; and
   irradiating the spinal cord injury site with the laser light carried via the optical wire, the optical wire and the light emission surface are positioned subcutaneously.

2. The method of claim 1, wherein the light emission surface is positioned within 2 centimeters of the spinal cord injury site.

3. The method of claim 1, wherein the light emission surface is positioned within 1 centimeter of the spinal cord injury site.

4. The method of claim 1 wherein at least a portion of the optical wire and the light emission surface are positioned in epidural space of a human spinal canal.

5. The method of claim 1, further comprising implanting the source of laser light within the human body.

6. The method of claim 1, wherein the source of laser light selectively emits a laser light having a wavelength selected from one of multiple selectable wavelengths.

7. The method of claim 1, wherein the source of laser light selectively emits a laser light having a power selected from one of multiple selectable power levels.

8. The method of claim 1, wherein the optical wire comprises a plurality of optical fibers grouped together.

9. The method of claim 8, wherein a number of optical fibers in the plurality of optical fibers is between 10 and 100.

10. The method of claim 9, further comprising emitting the laser light using a fenestrated tip.

11. The method of claim 10, further comprising a sheath that covers the optical fibers from the first end of the optical fibers to the second end of the optical fibers.

12. The method of claim 10, wherein the fenestrated tip has an emission surface for emission of laser light from each of the optical fibers.

13. The method of claim 12, wherein the fenestrated tip includes emission surfaces adapted for emitting the laser light at an angle relative to a longitudinal axis of the fenestrated tip.

14. The method of claim 13, wherein the fenestrated tip includes a rounded end that defines light emission openings in the fenestrated tip, the light emission openings configured to emit a plurality of laser light beams in a spreading axial pattern relative to the fenestrated tip.

15. The method of claim 13, wherein the fenestrated tip includes a sidewall that defines light emission openings in the fenestrated tip, the light emission openings configured to emit a plurality of laser light beams from the sidewall.

16. The method of claim 1 further comprising disposing the light emission surface in an epidural space between the dura mater and the spinal cord of a patient such that the windows of the light emission surface are disposed pointed toward the spinal cord injury site.

17. The method of claim 1 further comprising disposing the light emission surface in an epidural space between the dura mater and the spinal cord of a patient such that the windows of the light emission surface are disposed pointed toward the spinal cord injury site.

* * * * *